United States Patent [19]

Masaki et al.

[11] 3,962,178

[45] June 8, 1976

[54] STABILIZED POLYOLEFIN COMPOSITION

[75] Inventors: Mitsuo Masaki; Satoshi Matsunami; Toshio Yoshikawa; Nagayoshi Sakamoto, all of Ichihara, Japan

[73] Assignee: UBE Industries, Ltd., Ube, Japan

[22] Filed: July 16, 1975

[21] Appl. No.: 596,516

[30] Foreign Application Priority Data

Aug. 6, 1974   Japan.............................. 49-89465

[52] U.S. Cl...................... 260/45.75 W; 260/42.46; 260/45.85 B
[51] Int. Cl.²............................................. C08J 3/20
[58] Field of Search............................ 260/45.75 W

[56] References Cited
UNITED STATES PATENTS

| | | | |
|---|---|---|---|
| 2,997,456 | 8/1961 | Mills........................... | 260/45.75 W |
| 3,723,435 | 3/1973 | Furia et al..................... | 260/45.75 R |
| 3,850,883 | 11/1974 | Masaki et al.................. | 260/45.75 K |
| 3,862,151 | 1/1975 | Furia et al..................... | 260/45.75 R |

*Primary Examiner*—V.P. Hoke
*Attorney, Agent, or Firm*—Flynn & Frishauf

[57] ABSTRACT

A polyolefin composition containing a novel 2-pyridylthiozinc-oxide complex, hexakis(2-pyridylthio)-tetrazinc monooxide, has resistance against thermal and oxidative deterioration, particularly against deterioration caused by contact with heavy metals. Various processes for the preparation of said complex are also disclosed.

5 Claims, 3 Drawing Figures

STABILIZED POLYOLEFIN COMPOSITION

This invention relates to a polyolefin composition containing a novel 2-pyridylthiozinc-oxide complex, hexakis(2-pyridylthio) tetrazinc monooxide.

Heretofore, such polyolefins as polyethylene, polypropylene, polybutene and the like have been employed in a wide field owing to their excellent physical or chemical characteristics. However, as is commonly known, if a polyolefin is employed with no additives, it will be deteriorated by heat, light or oxygen during processing or with use. In order to prevent its deterioration, several kinds or anti-oxidizing agents have been developed and employed.

Yet, in cases where polyolefins cannot be kept from contact with such heavy metals as copper, iron, nickel and the like, for instance, in cases of covering a polyolefin over copper wire, plating a polyolefin with heavy metals, coloring a polyolefin by pigments containing heavy metals and the like, the use of the aforementioned general anitoxidizing agents can hardly bring about resistance against deterioration caused by contact with heavy metals.

Further, if a liquid amorphous polyolefin may possibly contact copper, for instance, if a liquid amorphous polyolefin is employed as an insulating oil for a cable, there is required resistance against deterioration casused by contact with copper. Yet, the aforementioned general anti-oxidizing agents cannot meet the above requirement.

For the above reason, such anti-deteriorating agents as MARK-CDA-1 (Adaka-Argus Chemical Industry Co., Ltd.), N,N'-dibenzylideneoxalic acid dihydrazide, N-salicylidenesalicylic acid hydrazide and the like have been developed and broadly empolyed for the purpose of imparting a polyolefin resistance against deterioration caused by contact with heavy metals. Nevertheless, these agents cannot be mentioned as agents satisfying the requirement of anti-deterioration effect.

Therefore, one object of this invention is to provide a polyolefin composition having resistance against deterioration caused by contact with heavy metals. Other objects of this invention will be obvious from the contents of the specification hereinafter disclosed.

The novel 2-pyridylthiozinc-oxide complex herein disclosed is hexakis(2-pyridylthio)tetrazinc monooxide having the formula

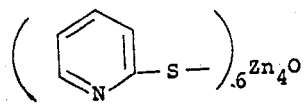

Based on numbers of the 2-pyridylthio group, zinc atom and oxygen atom, the above-mentioned hexakis(2-pyridylthio)tetrazinc monooxide may possibly be illustrated by the following two structural formulae.

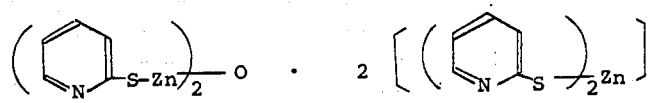

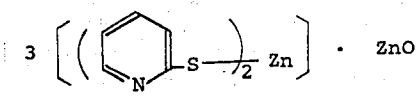

However, these structural formulae are illustrated on assumption only, and are not limiting the present compound.

According to this invention, hexakis(2-pyridylthio)-tetrazinc monooxide may be prepared by several modes of reactions from bis(2-pyridylthio)zinc or 2-pyridinethiol. Details of the reactions are disclosed below.

Reaction of Bis(2-pyridylthio)zinc with Water

The present reaction may be illustrated as follows.

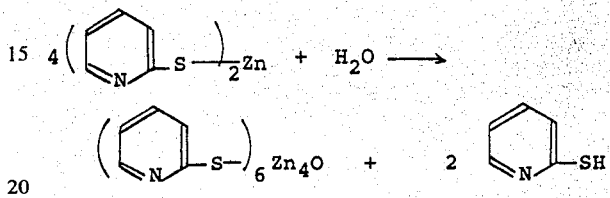

Water charged into the reaction system may be in an amount of from the amount needed (stoichiometrical amount) to a large amount enough for the reaction medium. In this reaction, an organic solvent dissolving 2-pyridinethiol by-product may be employed in conjunction with the water. Such a solvent may be exemplified by an aromatic hydrocarbon and its halogenated derivative, e.g., benzene, toluene, xylene, chlorobenzene and chlorotoluene, a halogenated aliphatic hydrocarbon, e.g., methylene chloride, ethylene dichloride and chloroform, an alcohol, e.g., methanol, ethanol, propanol, butanol and hexanol, a ketone, e.g., acetone and methyl ethyl ketone, an ether, e.g., ethyl ether, tetrahydrofuran and dioxane, acetonitrile, dimethylformamide and dimethylsulfoxide.

The present reaction is a reversible one, and if bis(2-pyridylthio)zinc and water are reacted at 80°C in the stoichiometrical amount, namely in a molar ratio of 4 : 1, the reaction reaches an equilibrium state when approximately 30% of bis(2-pyridylthio)zinc is converted into the 2-pyridylthiozinc-oxide complex. In the reaction mixture at this stage, bis(2-pyridylthio)-zinc, water, the 2-pyridylthiozinc-oxide complex and 2-pyridinethiol are present in a molar ratio of approximately 28 : 7 : 3 : 6, respectively, as shown in Reference example 1. The above statement to the effect that the said state is in equilibrium has been provided by the experiment shown in Reference example 2: that is, the reaction of the 2-pyridylthiozinc-oxide complex with 2-pyridinethiol in a molar ratio of 1 : 2, which is a reverse reaction of the above-stated reaction, has been performed at 80°C to give the mixture consisting of the four components in the same molar ratio as in the above-mentioned reaction mixture.

Hence, in order to obtain the 2-pyridylthiozinc-oxide complex from bis(2-pyridylthio)zinc and water in good yield, the following two procedures are preferably proposed.

A. Procedure employing an excess amount of water, and/or
B. Procedure accompanied by removal of by-product 2-pyridinethiol during the reaction According to Procedure (A), when water is employed in an amount more than four times by weight as much as that of bis(2-pyridylthio)zinc, the charged bis(2-pyridylthio)zinc is almost completely converted into the 2-pyridylthiozinc-oxide complex. According to Procedure (B), when the reaction is conducted with removing by-procuct 2-pyridinethiol out of the reaction mixture during the reaction, by way of, for instance, extraction, the charged bis(2-pyridylthio)zinc is almost completely converted into the 2-pyridylthiozinc-oxide complex, provided the charged water is in an amount corresponding to, at least, the stoichiometrical amount. Procedures (A) and (B) may, of course, be jointly adopted. The reaction period varies dependent upon the reaction temperature and the amount of water. That is, the higher the reaction temperature is, the shorter the reaction period is. Further, the more the amount of water is, the shorter the reaction period is. Ordinarily, the reaction temperature ranges from 40° to 150°C, and under such conditions the reaction period is between a few minutes and 50 hours. The reaction may proceed below the above-limited lower temperature, but the reaction rate for conversion of bis(2-pyridylthio)zinc into the 2-pyridylthiozinc-oxide complex extremely decreases so that longer reaction period may be required. For instance, the reaction at 30°C for 50 hours gives, even if water in an amount 20 times by weight as much as that of the bis(2-pyridylthio)zinc is employed, approximately 25% of the conversion ratio based on the employed bis(2-pyridylthio)zinc, as disclosed in Reference example 4.

In case the reaction is carried out at the temperature and for the period within the range specified above and under the conditions of the procedures (A) and/or (B), there hardly is found unreacted bis(2-pyridylthio)zinc in the reaction mixture obtained. Therefore, as a solid, only the 2-pyridylthiozinc-oxide complex which is insoluble or sparingly soluble in either water or the aforementioned organic solvent is present in the reaction mixture. Then the said 2-pyridylthiozinc-oxide complex is easily isolated by the procedure such as filtration and centrifugation.

However, in certain cases and under certain conditions, unreacted bis(2-pyridylthio)zinc may remain in the reaction mixture, and hence the reaction product isolated by filtration or centrifugation may be contaminated with the bis(2-pyridylthio)-zinc. In that case, the 2-pyridylthiozinc-oxide complex may be isolated by extracting or washing the isolated mixture with such a solvent as benzene and acetonitrile to remove the bis(2-pyridylthio)zinc.

Reaction of Bis(2-pyridylthio)zinc with Water in the presence of Base

The present reaction may be illustrated as follows.

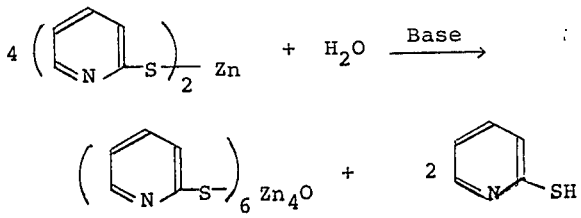

Water charged into the reaction system may be in an amount needed (stoichiometrical amount) to a large amount enough for the reaction medium. In this reaction, an organic solvent such as an aromatic hydrocarbon and its halogenated derivative, e.g., benzene, toluene, xylene, chlorobenzene and chlorotoluene, a halogenated aliphatic hydrocarbon, e.g., methylene chloride, ethylene dichloride and chloroform, an alcohol, e.g., methanol, ethanol, propanol, butanol and hexanol, a ketone, e.g., acetone and methyl ethyl ketone, an ether, e.g., ethyl ether, tetrahydrofuran and dioxane, acetonitrile, dimethylformamide and dimethylsulfoxide may be employed in conjunction with the water.

The present reaction likewise is a reversible one in the same sense as stated in the previous reaction. Hence, in order to obtain the 2-pyridylthiozinc-oxide complex from bis(2-pyridylthio)zinc and water in good yield, such procedures as described in the aforementioned reaction may preferably be proposed, that is,
A. Procedure employing an excess amount of water, and/or
B. Procedure accompanied by removal of by-produced 2-pyridinethiol during the reaction.

Detailed description of such procedures are set forth hereinbefore.

Figure 1:
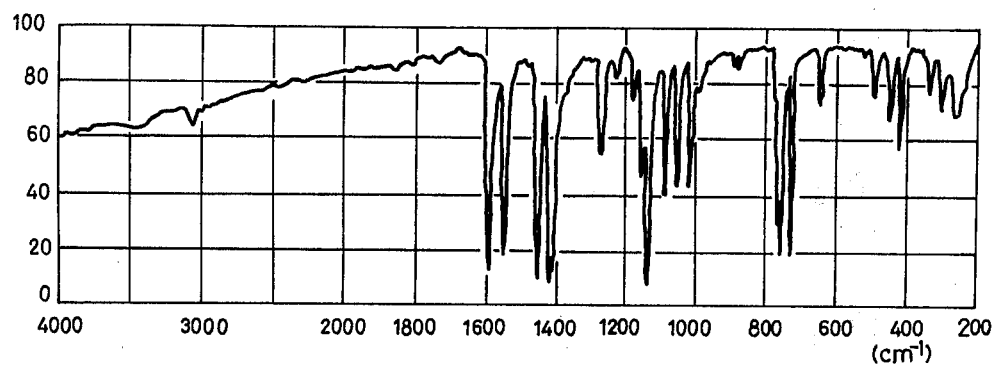

The present reaction is carried out in the presence of a base so as to obtain the 2-pyridylthiozinc-oxide complex from bis(2-pyridylthio)zinc in good yield. Said base may be exemplified by an inorganic base such as potassium hydroxide, sodium hydroxide, potassium carbonate, sodium carbonate, potassium oxide, sodium oxide and ammonia, and an organic base such as trimethylamine, triethylamine, triethanolamine, N-methylpiperidine, N-methylpyrrolidine, N,N-diethylaniline, N,N-dimethyl-o-toluidine, pyridine, methylpyridine, ethylpyridine, aminopyridine, acridine, 1,8-bis(dimethylamino)-naphthalene and triethylenediamine. The amount of such a base to be added may be within 0.05 – 0.5 gram equivalent, that is, 0.05 – 0.5 mole for a monoacid base and 0.025 – 0.25 mole for a diacid base, based on one mole of the employed bis(2-pyridylthio)zinc. In case the added amount is above the said upper limit, side-reactions may take place, and in case the amount is below the lower limit, the addition of a base may hardly bring about enough effect.

It may be assumed that a base to be employed in the present process brings about an increase of the reaction rate. Further, in case the base forms a salt with the by-product 2-pyridinethiol, an amount of free 2-pyridinethiol decreases in the reaction system whereby the aforementioned reversible reaction is inclined to produce the 2-pyridylthiozinc-oxide complex.

In the present process employing a base and utilizing the aforementioned procedures (A) and/or (B), the reaction period needed for almost complete conversion of bis(2-pyridylthio)zinc into the 2-pyridylthiozinc-oxide complex may vary dependent upon the reaction temperature, the amount of water and the kind and amount of the base. Ordinarily, the higher the reaction temperature is, the more the amount of water is, and, within the above range, the more the amount of the base is, the shorter the reaction period is. The reaction temperature may conveniently be within 0°–150°C. Under the said conditions, the reaction period may be between a few minutes and 50 hours. The reaction may proceed below the above-limited lower temperature, but the reaction rate extremely decreases so that longer reaction period is required.

In case the reaction is carried out at the temperature and for the period within the range specified above in the presence of a base and further under the conditions of the procedures (A) and/or (B), there hardly is found unreacted bis(2-pyridylthio)-zinc in the reaction mixture obtained. Therefore, after completion of the reaction, solids in the reaction mixture are of either the 2-pyridylthiozinc-oxide complex alone or a mixture of the 2-pyridylthiozinc-oxide complex and a salt of the employed base with by-produced 2-pyridinethiol precipitated from the water or the organic solvent. In the former case, the 2-pyridylthiozinc-oxide complex may be isolated by the procedure such as filtration and centrifugation. In the latter case, the 2-pyridylthiozinc-oxide complex can be isolated by the procedure such as filtration and centrifugation and then washihg with either water or an organic solvent dissolving the salt.

However, in certain cases and under certain conditions, unreacted bis(2-pyridylthio)zinc may remain in the reaction mixture. In these cases, such procedures as disclosed in the aforementioned reaction may be adopted.

by an aromatic hydrocarbon and its halogenated derivative, e.g., benzene, toluene and xylene, aliphatic and alicyclic hydrocarbons, e.g., hexane, heptane and cyclohexane, halogenated derivatives of aliphatic and alicyclic hydrocarbons, e.g., methylene chloride, ethylene dichloride, chloroform and carbon tetrachloride, a ketone, e.g., acetone and methyl ethyl ketone, an alcohol, e.g., methanol, ethanol and butyl alcohol, an ether, e.g., diethyl ether, dioxane, tetrahydrofuran and diglyme, acetonitrile, dimethylformamide and dimethylsulfoxide. The reaction temperature may ordinarily be within 10° – 120°C. The reaction may proceed below 10°C, but such a reaction temperature is not preferred due to a longer reaction period. The reaction period may vary dependent upon the reaction temperature, the scale of the reaction and the like, and it may ordinarily be between 30 minutes and 100 hours. In addition, the present reaction is preferably effected with stirring.

Reaction of 2-Pyridinethiol with Zinc Oxide or Zinc Hydroxide

The present reaction may be illustrated as follows.

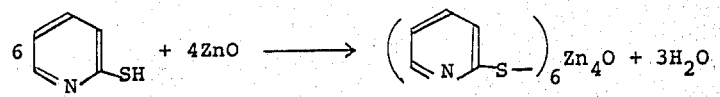

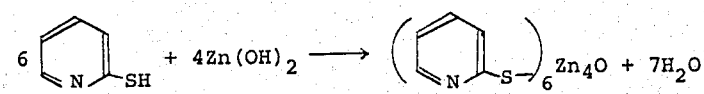

Reaction of Bis(2-pyridylthio)zinc with Zinc Oxide or Zinc Hydroxide

The present reaction may be illustrated as follows.

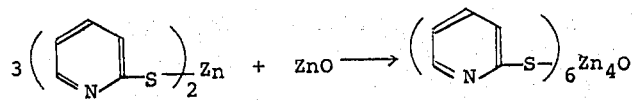

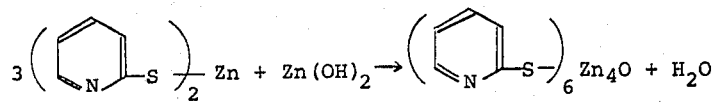

In this reaction, bis(2-pyridylthio)zinc and zinc oxide (or zinc hydroxide) may preferably be charged in a molar ratio of approximately 3 : 1, respectively, and the reaction may preferably be performed in a certain solvent.

In case the molar ratio of bis(2-pyridylthio)zinc to zinc oxide (or zinc hydroxide) is, as mentioned above, 3 : 1, the reaction gives almost only the 2-pyridylthiozinc-oxide complex. Therefore, the above-mentioned molar ratio may preferably be adopted. The desired complex may be obtained by the reaction employing the starting compounds in other molar ratios. But, in such cases, the starting compounds may in part get mixed in the reaction product, and such molar ratios, therefore, are not preferred. For the reasons stated above, the molar ratio is preferred to be either 3 : 1 or around 3 : 1.

The reaction solvent employed may be water or an organic solvent which is utilized in the usual chemical reaction. Such an organic solvent may be exemplified In this reaction, 2-pyridinethiol and zinc oxide (or zinc hydroxide) may preferably be charged in a molar ratio of approximately 6 : 4, respectively, and the reaction may preferably be performed in a certain solvent. pressure piece.

In case the molar ratio of 2-pyridinethiol to zinc oxide (or zinc hydroxide) is, as mentioned above, 6 : 4, the reaction gives almost only the 2-pyridylthiozinc-oxide complex. Therefore, the above-mentioned molar ratio may preferably be adopted. The desired complex may be obtained by the reaction employing the starting compounds in other molar ratios. But, in case 2-pyridinethiol is charged in an excess amount, 2-pyridinethiol further may, under certain circumstances, react with the resulting product (desired compound) to give a by-product in the following manner.

For this reason, the molar ratio is preferred to be either 6 : 4 or around 6 : 4.

There is no specific limitation on the reaction solvent, so far as it can dissolve 2-pyridinethiol. Such a solvent may be an organic solvent, for instance, a halogenated hydrocarbon, a ketone, a nitrile, a dialkylformamide, a dialkylsulfoxide and an aromatic hydrocarbon. The preferred solvent may be a halogenated aliphatic hydrocarbon, e.g., methylene chloride, ethylene dichloride, chloroform and carbon tetrachloride, a ketone, e.g., acetone and methyl ethyl ketone, or a nitrile, e.g., acetonitrile. An alcohol such as methanol and ethanol and an ether such as ethyl ether and dioxane are not preferred as the reaction solvent industrially employed, because these solvents ordinarily give relatively low reaction yields and cause side-reactions.

The present reaction is performed at a temperature below the decomposition point of 2-pyridinethiol, and the reaction temperature may oridinarily be within 10° − 120°C. The reaction period may vary dependent upon the reaction temperature, the scale of the reaction and the like, and it may ordinarily be bewteen 10 minutes and 30 hours. In addition, the present reaction is preferably effected with stirring.

Reaction of 2-Pyridinethiol with Zinc Salt

The present reaction is conducted by reacting 2-pyridinethiol with a zinc salt in the presence of a base and water. This reaction may be illustrated by employing as the zinc salt, for instance, $ZnX_2$, as follows.

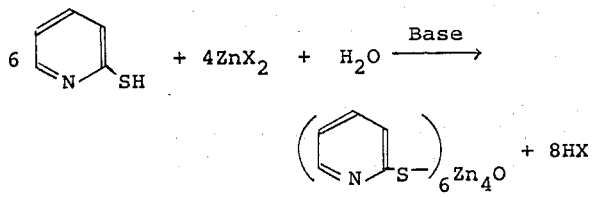

In the present reaction, the phrase "the presence of water" includes the following conditions:
1. Addition of water to the reaction system,
2. Employment of a solvent and/or the starting compounds containing water (water may be contained in the form of water of crystallization.), and
3. Utilization of water produced during the some reaction system, which is, for instance, as follows:

```
   6PySH + 6NaOH  →  6PySNa + 6H₂O
   6PySNa + H₂O   →  (PyS)₆Zn₄O + 2H₂O + 8NaCl
                    + 2NaOH + 4ZnCl₂
+) ─────────────────────────────────────────────
   6PySH + 8NaOH + 4ZnCl₂ → (PyS)₆Zn₄O + 8NaCl + 7H₂O
```
NOTE: PySH 2-pyridinethiol According to this reaction, in case 2-pyridinethiol and a zinc salt are employed in a molar ratio of 3 : 2 and a base is employed in just or around two gram equivalents based on one mole of the zinc salt, the reaction gives almost only the 2-pyridylthiozinc-oxide complex. The reaction may proceed in the presence of a base of more than the above-mentioned amount. However, in view of probability of side-reactions taking place, the amount of the base may preferably be not more than four gram equivalents based on one mole of the zinc salt.

The desired complex may be obtained by reactng the starting compounds in other molar ratio. However, in case a molar ratio far from 3 : 2 is applied, the reaction may possibly be accompanied by side-reactions or give lower yield. For this reason, the above-mentioned stoichiometrical amount (2-pyridinethiol : zinc salt = 3 : 2) or an amount in the vicinity of that amount may preferably be applied.

In addition, water to be present in this reaction is in an amount more than one sixth mole as much as that of 2-pyridinethiol, and may be in amount enough for a solvent.

There is no specific limitation on the zinc salt employed as the starting material in this reaction, so far as it is a divalent zinc salt. Such a zinc salt may be an inorganic or organic zinc salt exemplified by zinc chloride, zinc bromide, zinc sulfate, zinc nitrate and zinc acetate. Said salt may be in the form of an anhydride or a hydrated salt. There is likewise no specific limitation on the base, which may preferably be exemplified as follows: an inorganic base such as a hydroxide of an alkali metal, e.g., sodium hydroxide and potassium hydroxide, a carbonate of an alkali metal, e.g., sodium carbonate and potassium carbonate and a hydrogen carbonate of an alkali metal, e.g., sodium hydrogen carbonate, potassium hydrogen carbonate, and ammonia, or an organic base such as a lower alkylamine, e.g., triethylamine and trimethylamine, a lower alkanolamine, e.g., triethanolamine, and an aromatic or heterocyclic amine, e.g., N-methylpiperidine, N-methylpyrrolidine, N,N-diethylaniline, N,N-dimethyl-o-toluidine, pyridine, methylpyridine, aminopyridine, acridine, 1,8-bis(dimethylamino)naphthalene, triethylenediamine and ethylpyridine.

The present reaction is ordinarily performed in a solvent. The solvent may be water or a solvent that can be miscible with water participating in the process and that can, in such an aqueous solvent state, wholly or partly dissolve 2-pyridinethiol, the zinc salt and the base. Such a solvent may concretely be exemplified by dimethylformamide, dimethylsulfoxide, a lower alcohol such as methanol, ethanol and propanol, and a ketone such as acetone and methyl ethyl ketone.

The reaction temperature may vary dependent upon the kinds and molar ratios of the reactants and the solvent, and ordinarily is within 0° − 120°C. The reaction period may vary dependent upon the reaction conditions, and ordinarily is between a few minutes and 20 hours.

The 2-pyridylthiozinc-oxide complex, hexakis(2-pyridylthio)tetrazinc monooxide, can impart stabilization, particularly resistance against deterioration caused by contact with heavy metals, to a polyolefin when it is incorporated into the polyolefin in an amount of 0.001 − 5 weight parts based on 100 weight parts of the polyolefin. Said polyolefin may be exemplified by amorphous, crystalline or liquid homopolymers or copolymers of olefins such as ethylene, propylene, butene-1, isobutene, pentene-1 and 4-methylpentene-1, copolymers of these olefins and alkylesters of unsaturated carboxylic acids such as methyl acrylate, ethyl acrylate, methyl methacrylate and ethyl methacrylate or vinylesters of saturated carboxylic acids such as vinyl acetate, and mixtures of these polymers.

Accordingly, the present invention provides a stabilized polyolefin composition which comprises 100 weight parts of a polyolefin and 0.001 − 5 weight parts, preferably 0.01 − 3 weight parts, of hexakis(2-pyridylthio)tetrazinc monooxide having the formula

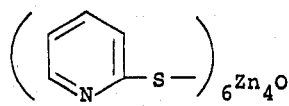$_6Zn_4O$

In case the amount of the said zinc complex is less than the said lower limit, 0.001 weight part, the effect against deterioration is not enough. Further, even if the said amount is more than the said upper limit, 5 weight parts, the said anti-deterioration effect no more increases.

Every process adequate for the preparation of a homogeneous composition may be adapted to a process for mixing or compounding of the aforementioned 2-pyridylthiozinc-oxide complex into a polyolefin. Such a process may be exemplified by a process which comprises dissolving or dispersing the zinc complex in a low-boiling solvent, mixing the solution or dispersion with a polyolefin and removing the solvent by evaporation, a process which comprises heating a polyolefin to a temperature above its melting point and then compounding the zinc-complex thereinto, or a process which comprises mixing a polyolefin with the zinc complex by means of one of several mixers.

Further, the 2-pyridylthiozinc-oxide complex provided by this invention may be employed together with a publicly known stabilizer, dispersing agent, plasticizer, anti-static agent, filler and/or pigment.

Such a known stabilizer may be exemplified by a phenol-type compound, for instance, 2,6-di-tert-butyl-p-cresol, 2,6-di-tert-butylphenol, 4,4'-methylenebis(2,6-di-tert-butylphenol), 4,4'-methylenebis(3-methyl-6-tert-butylphenol), 4,4'-bis(2,6-di-tert-butylphenol), 4,4'-thiobis(2-methyl-6-tert-butylphenol), 6-(4-hydroxy-3,5-di-tert-butylanilino)-2,4-bis(n-octylthio)-1,3,5-triazine, tetrakis [methylene 3-(3,5-di-tert-butyl-4-hydroxyphenyl)-propionate]methane, octadecyl-3-(3,5-di-tert-butyl-4-hydroxyphenyl)propionate, 1,1,3-tris(2-methyl-4-hydroxy-5-tert-butylphenyl)butane, 2,2'-methylenebis(4-methyl-6-tert-butylphenol), 4,4'-butylidenebis(3-methyl-6-tert-butylphenol), 2,2'-methylenebis-(4-ethyl-6-tert-butylphenol) and 1,3,5-trimethyl-2,4,6-tris(3,5-di-tert-butyl-4-hydroxybenzyl)benzene, a 3,3'-thiodipropionic acid dailkylester, for instance, didodecyl 3,3'-thiodipropionate and dioctadecyl 3,3'-thiodipropionate and an organic phosphorous compound, for instance, trilaurylphosphite, trilauryl trithiophosphite and tris(nonylphenyl)phosphite.

The present invention will be illustrated in more detail in the following examples, but the said examples are not intended to limit the present invention.

Preparation of bis(2-pyridylthio)zinc

Bis(2-pyridylthio)zinc, one of the starting compounds, was prepared as follows:

In a mixture of 525 ml of 1N aqueous sodium hydroxide solution and 400 ml of water was dissolved 61.00 g of 2-pyridinethiol. To this solution was added dropwise 300 ml of water containing 39.36 g of zinc chloride, and the resulting mixture was stirred at 20°C for 3 hours. The reaction mixture was then filtered off, washed with one liter of water and dried. There was obtained 74.25 g of bis(2-pyridylthio)zinc as slightly yellowish colorless crystals. The crystals gradually decomposed at about 240°C.

Found: C, 41.84%; H, 2.76%; N, 9.67%; S, 22.25%.
Calcd. for $C_{10}H_8N_2S_2Zn$: C, 42.04%; H, 2.82%; N, 9.81%; S, 22.45%.

Infrared spectrum of the obtained crystals was determined in the form of a KBr tablet by means of Infrared Grating Spectrograph 225 type (prepared by Hitachi Ltd., Japan) and is shown in the attached FIG. 1.

EXAMPLE 1

In 300 ml of water was suspended 30.00 g of bis(2-pyridylthio)zinc, and the suspension was refluxed with heating for 30 minutes and cooled to room temperature(approximately 25°C). The reaction mixture was then filtered (Filtration I), and the collected product was again suspended in 300 ml of water. The suspension was refluxed with heating for 30 minutes and cooled to room temperature. The reaction mixture was then filtered (Filtration II), and the collected product was washed with 100 ml of water and dried. There was obtained 24.44 g of hexakis(2-pyridylthio)tetrazinc monooxide as colorless powdery crystals. The obtained crystals began coloring gradually at about 340°C, and decomposed and melted at 380° – 385°C.

Found: C, 38.41%; H, 2.51%; N, 8.80%; S, 20.25%; Zn, 27.40%.
Calcd. for $C_{30}H_{24}N_6OS_6Zn_4$: C, 38.40%; H, 2.58%; N, 8.96%; S, 20.50%; Zn, 27.87%.

The crystals as obtained were insoluble or sparingly soluble in all of petroleum ether, petroleum benzine, n-hexane, ligroin, benzene, toluene, chloroform, carbon tetrachloride, ethylene dichloride, ethyl acetate, acetonitrile, methanol, ethanol, n-butanol, isopropyl alcohol and n-hexanol in hot or cooled states. Further the crystals were slightly soluble in hot nitrobenzene and soluble to a certain degree in dimethylsulfoxide and dimethylformamide; solubilities at 25°C were 0.8 g/100 g and 0.4 g/100 g, respectively.

Figure 2:
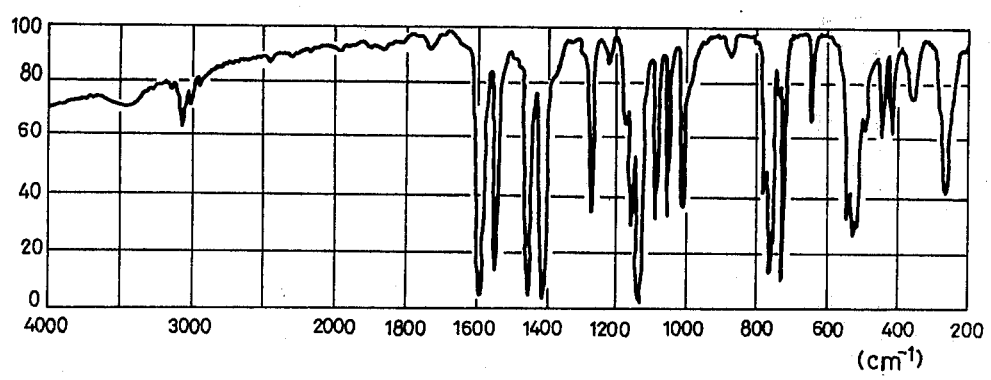
Figure 3:
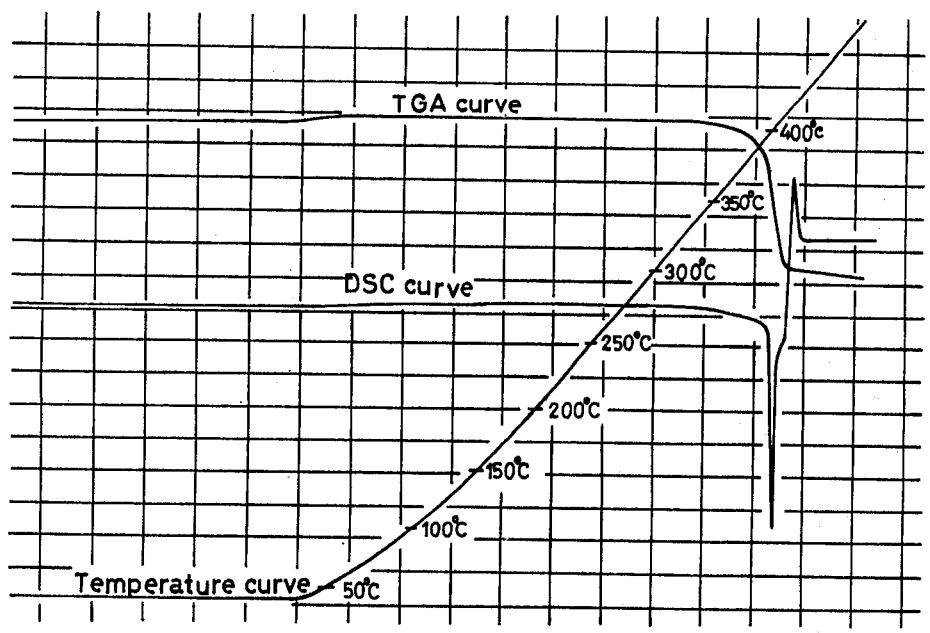

Infrared spectrum of the obtained crystals was determined in the form of a KBr tablet by means of the Infrared Grating Spectrograph 225 type and is shown in the attached FIG. 2. In addition, differential thermal analysis curves (TGA curve for weight change and DSC curve for heat capacity) were determined by means of Differential Thermal Balance 8085 type (prepared by Rigaku Denki Kogyo Co., Ltd., Japan) under conditions of 10°C/min. of the temperature elevation rate and in air, and are shown in the attached FIG. 3.

The filtrates obtained in the aforementioned Filtrations I and II were combined and concentrated under reduced pressure so as to remove water. To the residue was added 100 ml of acetone, and the mixture was stirred for 10 minutes and filtered leaving the insoluble materials. The obtained filtrate was concentrated under reduced pressure to yield 5.70 g of 2-pyridinethiol as yellow crystals, m.p. 124° – 126°C.

EXAMPLE 2

In 100 ml of water was suspended 5.71 g of bis(2-pyridylthio)zinc, and the suspension was stirred in an oil bath at 80°C for 15 minutes. The reaction mixture was then cooled to room temperature in a cold water bath and filtered. The collected product was washed with two portions of 20 ml of water and dried to yield 4.67 g of hexakis(2-pyridylthio)-tetrazinc monooxide as colorless powdery crystals. The crystals so obtained began coloring gradually at about 340°C, and decomposed and melted at 380° – 385°C.

Found: C, 38.52%; H, 2.52%; N, 9.25%; S, 20.80%; Zn, 27.45%.

The crystals so obtained were identical to the crystals obtained in Example 1 in the solubilities, IR spectrum and the TGA and DSC curves.

The filtrate and washings obtained in the aforementioned filtration were combined and concentrated under reduced pressure. To the residue was added 100 ml of acetone, and the mixture was stirred for 10 minutes and filtered leaving the insoluble materials. The filtrate so obtained was concentrated under reduced pressure to yield 1.09 g of 2-pyridinethiol as yellow crystals, m.p. 127° – 128°C.

EXAMPLE 3

In 100 ml of water was suspended 5.71 g of bis(2-pyridylthio)-zinc, and the suspension was heated in an oil bath of a temperature of 120°C. The suspension began refluxing after 12 minutes from the beginning of the heating. After refluxing by heating for 5 minutes, the reaction mixture was cooled to room temperature in a cold water bath and filtered. The collected product was washed with two portions of 20 ml of water and dried to yield 4.62 g of hexakis(2-pyridylthio)tetrazinc monooxide as colorless powdery crystals.

The crystals so obtained began coloring gradually at about 340°C, and decomposed and melted at 380° – 385°C.

Found: C, 38.42%; H, 2.52%; N, 8.74%; S, 20.27%; Zn, 27.60%.

The crystals so obtained were identical to the crystals obtained in Example 1 in the solubilities, IR spectrum and the TGA and DSC curves.

The filtrate and washings obtained in the aforementioned filtration were combined and concentrated under reduced pressure. To the residue was added 100 ml of acetone, and the mixture was stirred for 10 minutes and filtered leaving the insoluble materials. The filtrate so obtained was concentrated under reduced pressure to yield 1.10 g of 2-pyridinethiol as yellow crystals, m.p. 126° – 127°C.

EXAMPLE 4

In a mixture of 22.84 g of water and 100 ml of 1,4-dioxane was suspended 5.71 g of bis(2-pyridylthio)-zinc, and the suspension was stirred at 80°C for 4 hours. The reaction mixture was then cooled to room temperature in a cold water bath and filtered. The collected product was washed with two portions of 20 ml of 1,4-dioxane and dried to yield 4.65 g of hexakis(2-pyridylthio)tetrazinc monooxide as colorless powdery crystals. The crystals so obtained began coloring gradually at about 340°C, and decomposed and melted at 380° – 385°C.

Found: C, 38.74%; H, 2.66%; N, 8.67%; S, 20.18%; Zn, 27.75%.

The crystals so obtained were identical to the crystals obtained in Example 1 in the solubilities, IR spectrum and the TGA and DSC curves.

The filtrate and washings obtained in the aformentioned filtration were combined and concentrated under reduced pressure. To the residue was added 100 ml of acetone, and the mixture was stirred for 10 minutes and filtered leaving the insoluble materials. The filtrate so obtained was concentrated under reduced pressure to yield 1.11 g of 2-pyridinethiol as yellow crystals, m.p. 127° – 128°C.

EXAMPLE 5

In a mixture of 0.9 g of water and 100 ml of 1,4-dioxane was suspended 5.71 g of bis(2-pyridylthio)zinc, and the suspension was stirred at 80°C for 14.5 hours. The reaction mixture was then cooled to room temperature in a cold water bath and filtered (Filtration I). The collected product was washed with two portions of 20 ml of 1,4-dioxane and dried to yield 4.80 g of colorless crystals. The crystals were identified as mixtures of bis(2-pyridylthio)zinc and hexakis(2-pyridylthio)-tetrazinc monooxide by the IR spectrum. In a mixture of 16.00 g of water and 100 ml of 1,4-dioxane was suspended 4.73 g of the crystals so obtained, and the suspension was stirred at 80°C for 4 hours. The reaction mixture was then cooled to room temperature and filtered (Filtration II). The collected product was washed with two portions of 20 ml of 1,4-dioxane and dried to yield 4.45 g of hexakis(2-pyridylthio)tetrazinc monooxide as colorless powdery crystals. The crystals so obtained began coloring gradually at about 340°C, and decomposed and melted at 380° – 385°C.

Found: C, 38.58%; H, 2.63%; N, 8.71%; S, 20.23%; Zn, 27.80%.

The crystals so obtained were identical to the crystals obtained in Example 1 in the solubilities, IR spectrum and the TGA and DSC curves.

The filtrate and washings obtained in the aforementioned Filtration I were combined and concentrated under reduced pressure. To the residue was added 100 ml of acetone, and the mixture was stirred for 10 minutes and filtered leaving the insoluble materials. The filtrate so obtained was concentrated under reduced pressure to yield 0.91 g of 2-pyridinethiol as yellow crystals, m.p. 126° – 127°C.

The filtrate and washings obtained in the aforementioned Filtration II were likewise treated to yield 0.19 g of 2-pyridinethiol.

EXAMPLE 6

In a Soxhlet's extractor, 5.71 g of bis(2-pyridylthio)-zinc contained in a filter paper thimble was extracted with a mixture of 0.90 g of water and 100 ml of n-butanol for 14.5 hours. The residue in the thimble was dried to give 4.44 g of hexakis(2-pyridylthio)tetrazinc monooxide as colorless powdery crystals. The crystals so obtained began coloring gradually at about 340°C, and decomposed and melted at 380° – 385°C.

Found: C 38.07%; H, 2.43%; N, 8.76%; S, 20.17%; Zn, 27.91%.

The crystals so obtained were identical to the crystals obtained in Example 1 in the solubilities, IR spectrum and the TGA and DSC curves.

The extract was concentrated under reduced pressure, and 100 ml of acetone was added to the residue. After stirring for 10 minutes, the mixture was filtered leaving the insoluble materials. The filtrate so obtained was concentrated under reduced pressure to yield 1.10 g of 2-pyridinethiol as yellow crystals, m.p. 126° – .°C.

EXAMPLE 7

In 90 ml of water was suspended 5.71 g of bis(2-pyridylthio)zinc, and 10 ml of 1N aqueous sodium hydroxide solution was added to the suspension. After stirring at 20°C for 20 hours, the reaction mixture was filtered. The collected product was washed with two portions of 20 ml of water and dried to yield 4.64 g of hexakis(2-pyridylthio)tetrazinc monooxide as colorless powdery crystals. The crystals so obtained began coloring gradually at about 340°C, and decomposed and melted at 380° – 385°C.

Found: C, 38.11%; H, 2,48%; N, 8.89%; S, 20,21%; Zn, 28.04%.

The crystals so obtained were identical to the crystals obtained in Example 1 in the solubilities, IR spectrum and the TGA and DSC curves.

The filtrate and washing obtained in the aforementioned filtrations were combined and, after neutralization with 1N hydrochloric acid, concentrated under reduced pressure. To the residue was added 100 ml of acetone, and the mixture was stirred for 10 minutes and filtered leaving the insoluble materials. The filtrate so obtained was concentrated under reduced pressure to yield 1.05 g of 2-pyridinethiol, m.p. 127° – 128°C.

EXAMPLE 8

In 100 ml of an aqueous solution containing 0.56 g of potassium hydroxide was suspended 5.71 g of bis(2-pyridylthio)-zinc, and the suspension was stirred at 40°C for 12 hours. The reaction mixture was then cooled to 20°C and filtered. The collected product was washed with 100 ml of water and dried to yield 4.63 g of hexakis(2-pyridylthio)tetrazinc monooxide as colorless powdery crystals. The crystals so obtained began coloring gradually at about 340°C, and decomposed and melted at 380° – 385°C.

Found: C, 38.26%; H, 2.45Zn, 27.43%. N, 9.01%; S, 20.26%;

The crystals so obtained were identical to the crystals obtained in Example 1 in the solubilities, IR spectrum and the TGA and DSC curves.

The filtrate and washing obtained in the aforementioned filtration were combined and, after addition of 10 ml of 1N hydrochloric acid, concentrated under reduced pressure. To the residue was added 100 ml of acetone, and the mixture was stirred for 10 minutes and filtered leaving the insoluble materials. The filtrate so obtained was concentrated under reduced pressure to yield 1.07 g of 2-pyridinethiol, m.p. 125° – 128°C.

EXAMPLE 9

In a solution of 0.56 g of potassium hydroxide in a mixture of 0.91 g of water and 100 ml of ethanol was suspended 5.71 g of bis(2-pyridylthio)zinc, and the suspension was refluxed with heating for one hour. The reaction mixture was then cooled to 20°C and filtered. The collected product was washed with 20 ml of ethanol and 20 ml of water successively, and dried to yield 4.57 g of hexakis(2-pyridylthio)tetrazinc monooxide as colorless powdery crystals. The crystals so obtained began coloring gradually at about 340°C, and decomposed and melted at 380°– 385°C.

Found: C, 38.20%; H, 2.47%; N, 8.86%; S, 20.37%; Zn, 27.61%.

The crystals so obtained were identical to the crystals obtained in Example 1 in the solubilities, IR spectrum and the TGA and DSC curves.

The filtrate and washings obtained in the aforementioned filtration were combined and, after addition of 10 ml of 1N hydrochloric acid, concentrated under reduced pressure. To the residue was added 100 ml of acetone, and the mixture was stirred for 10 minutes and filtered leaving the insoluble materials. The filtrate so obtained was concentrated under residue pressure to yield 1.07 g of 2-pyridinethiol, m.p. 125°– 127°C.

EXAMPLE 10

In 90 ml of water was suspended 5.71 g of bis(2-pyridylthio)zinc, and, after addition of 10 ml of 1N aqueous sodium hydroxide solution, the mixture was stirred at 60°C for 2.5 hours. The reaction mixture was then cooled to 20°C and filtered. The collected product was washed with 100 ml of water and dried to yield 4.64 g of hexakis(2-pyridylthio)tetrazinc monooxide as colorless powdery crystals. The crystals so obtained began coloring gradually at about 340°C, and decomposed and melted at 380°– 385°C.

Found: C, 38.22%; H, 2.48%; N, 8.93%; S, 20.46%; Zn, 27.93%.

The crystals so obtained were identical to the crystals obtained in Example 1 in the solubilities, IR spectrum and the TGA and DSC curves.

The filtrate and washing obtained in the aforementioned filtration were combined and, after addition of 10 ml of 1N hydrochloric acid, concentrated under reduced pressure. To the residue was added 100 ml of acetone, and the mixture was stirred for 10 minutes and filtered leaving the insoluble materials. The filtrate so obtained was concentrated under reduced pressure to yield 1.10 g of 2-pyridinethiol, m.p. 126°– 128°C.

The procedure was repeated except for the addition of 1N aqueous sodium hydroxide solution and employing 8 hours of the reaction period. There were obtained 4.82 g of a mixture of bis(2-pyridylthio)zinc and hexakis(2-pyridylthio)tetrazinc monooxide as colorless powdery crystals and 0.85 g of 2-pyridinethiol. The identification of the mixture was made by IR spectrum of the product.

EXAMPLE 11

In 100 of an aqueous solution containing 0.056 g of potassium hydroxide was suspended 5.71 g of bis(2-pyridylthio)-zinc, and the suspension was stirred at 60°C for 8 hours. The reaction mixture was then cooled to 20°C and filtered. The collected product was washed with 100 ml of water and dried to yield 4.66 g of hexakis(2-pyridylthio)tetrazinc monooxide as colorless powdery crystals. The crystals so obtained began coloring gradually at about 340°C, and decomposed and melted at 380°– 385°C.

Found: C, 38.43%; H, 2.56%; N, 8.99%; S, 20.21%; Zn, 27.74%.

The crystals so obtained were identical to the crystals obtained in Example 1 in the solubilities, IR spectrum and the TGA and DSC curves.

The filtrate and washing obtained in the aforementioned filtration were combined and, after addition of 10 ml of 0.1N hydrochloric acid, concentrated under reduced pressure. To the residue was added 100 ml of acetone, and the mixture was stirred for 10 minutes and filtered leaving the insoluble materials. The filtrate so obtained was concentrated under reduced pressure to yield 1.03 g of 2-pyridinethiol.

EXAMPLE 12

In 100 ml of water was suspended 5.71 g of bis(2-pyridylthio)zinc, and, after addition of 0.53 g of sodium carbonate, the suspension was stirred at 60°C for 2.5 hours. The reaction mixture was then cooled on standing to 20°C and filtered. The collected product was washed with 100 ml of water and dried to yield 4.62 g of hexakis(2-pyridylthio)tetrazinc monooxide as colorless powdery crystals. The crystals so obtained began coloring gradually at about 340°C, and decomposed and melted at 380°– 385°C.

Found: C, 38.22%; H, 2.47%; N, 9.05%; S, 20.23%; Zn, 27.31%. The crystals so obtained were identical to the crystals obtained in Example 1 in the solubilities, IR spectrum and the TGA and DSC curves.

The filtrate and washing obtained in the aforementioned filtration were combined and, after addition of 10 ml of 1N hydrochloric acid, concentrated under reduced pressure. To the residue was added 100 ml of acetone, and the mixture was stirred for 10 minutes and filtered leaving the insoluble materials. The obtained filtrate was concentrated under reduced pressure to yield 1.06 g of 2-pyridinethiol, m.p. 126°– 128°C.

EXAMPLE 13

In a solution of 0.56 g of potassium hydroxide in a mixture of 22.84 g of water and 100 ml of 1,4-dioxane was suspended 5.71 g of bis(2-pyridylthio)zinc, and the suspension was stirred at 80°C for 30 minutes. The reaction mixture was then cooled to 20°C in cold water and filtered. The collected product was washed with 40 ml of water and 40 ml of 1,4-dioxane successively and dried to yield 4.61 g of hexakis(2-pyridylthio)tetrazinc monooxide as colorless powdery crystals. The crystals so obtained began coloring gradually at about 340°C, and decomposed and melted at 380°– 385°C.

Found: C, 38.56%; H, 2.63%; N, 8.89%; S, 20.25%; Zn, 27.52%.

The crystals so obtained were identical to the crystals obtained in Example 1 in the solubilities, IR spectrum and the TGA and DSC curves.

The filtrate and washings obtained in the aforementioned filtration were combined and, after addition of 10 ml of 1N hydrochloric acid, concentrated under reduced pressure. To the residue was added 100 ml of acetone, and the mixture was stirred for 10 minutes and filtered leaving the insoluble materials. The filtrate so obtained was concentrated under reduced pressure to yield 1.08 g of 2-pyridinethiol, m.p. 126°– 128°C.

EXAMPLE 14

To 100 ml of an aqueous suspension containing 5.71 g of bis(2-pyridylthio)zinc was added 1.01 g of triethylamine, and the mixture was stirred at 25°C for 30 hours and filtered. The collected product was then washed with 50 ml of water and dried to yield 4.63 g of hexakis(2-pyridylthio)tetrazinc monooxide as colorless powdery crystals. The crystals so obtained began coloring gradually at about 340°C, and decomposed and melted at 380°– 385°C.

Found: C, 38.66%; H, 2.61%; N, 8.93%; S, 20.30%; Zn, 27.64%.

The crystals so obtained were identical to the crystals obtained in Example 1 in the solubilities, IR spectrum and the TGA and DSC curves.

The filtrate and washing obtained in the aforementioned filtration were combined and concentrated under reduced pressure. To the residue was added 100 ml of acetone, and the mixture was stirred for 10 minutes and filtrated leaving the insoluble materials. The filtrate so obtained was concentrated under reduced pressure to yield 1.06 g of 2-pyridinethiol, m.p. 125°– 127°C.

EXAMPLE 15

In a mixture of 0.56 g of triethylenediamine, 8.00 g of water and 100 ml of 1,4-dioxane was suspended 5.71 g of bis(2-pyridylthio)zinc, and the suspension was stirred at 80°C for 4 hours. The reaction mixture was then cooled on standing to 20°C and filtered. The collected product was washed with two portions of 20 ml of 1,4-dioxane and dried to yield 4.61 g of colorless powdery crystals. The crystals so obtained began coloring gradually at about 340°C, and decomposed and melted at 380°– 385°C.

Found: C, 38.35%; H, 2.61%; N, 8.80%; S, 20.59%; Zn, 27.89%.

The crystals so obtained were identical to the crystals obtained in Example 1 in the solubilities, IR spectrum and the TGA and DSC curves.

The filtrate and washings obtained in the aforementioned filtration were combined and concentrated under reduced pressure. To the residue was added 100 ml of acetone, and the mixture was stirred for 10 minutes and filtered leaving the insoluble materials. The filtrate so obtained was concentrated under reduced pressure to yield 1.63 g of a mixture of 2-pyridinethiol and triethylenediamine.

EXAMPLE 16

In 300 ml of water were suspended 17.14 g of bis(2-pyridylthio)zinc and 1.62 g of zinc oxide, and the suspension was stirred at 100°C for 5 hours and filtered. The collected product was washed with five portions of 10 ml of water and dried to yield 18.52 g of hexakis(2-pyridylthio)tetrazinc monooxide as colorless powdery crystals. The crystals so obtained began coloring gradually at about 340°C, and decomposed and melted at 380°– 385°C.

Found: C, 38.19%; H, 2.52%; N, 8.96%; S, 20.58%; Zn, 27.57%.

The crystals so obtained were identical to the crystals obtained in Example 1 in the solubilities, IR spectrum and the TGA and DSC curves.

EXAMPLE 17

In 100 ml of acetonitrile were suspended 4.29 g of bis(2-pyridylthio)zinc and 0.41 g of zinc oxide, and the suspension was stirred at 82°C for 4 hours and filtered. The collected product was washed with four portions of 10 ml of acetonitrile and dried to yield 4.54 g of hexakis(2-pyridylthio)tetrazinc monooxide as colorless powdery crystals.

Found: C, 38.29%; H, 2.40%; N, 8.84%; S, 20.43%; Zn, 27.71%.

The crystals so obtained were identical to the crystals obtained in Example 1 in the melting point, the solubilities, IR spectrum and the TGA and DSC curves.

EXAMPLE 18

In 100 ml of benzene were suspended 4.29 g of bis(2-pyridylthio)zinc and 0.41 g of zinc oxide, and the mixture was stirred at 81°C for 5 hours. The reaction mixture was then filtered. The collected product was washed with two portions of 20 ml of benzene and dried to yield 4.66 g of hexakis(2-pyridylthio)-tetrazinc monooxide as colorless powdery crystals.

Found: C, 38.60%; H, 2.54%; N, 8.77%; S, 20.33%; Zn, 27.42%.

The crystals so obtained were identical to the crystals obtained in Example 1 in the melting point, the solubilities, IR spectrum and the TGA and DSC curves.

EXAMPLE 19

In 100 ml of ethanol were suspended 4.29 g of bis(2-pyridylthio)zinc and 0.41 g of zinc oxide, and the suspension was stirred at 79°C for 5 hours. The reaction mixture was then filtered. The collected product was washed with four portions of 10 ml of ethanol and dried to yield 4.48 g of hexakis(2-pyridylthio)-tetrazinc monooxide as colorless powdery crystals.

Found: C, 38.28%; H, 2.58%; N, 8.96%; S, 20.24%; Zn, 27.66%.

The crystals so obtained were identical to the crystals obtained in Example 1 in the melting point, the solubilities, IR spectrum and the TGA and DSC curves.

EXAMPLE 20

In 100 ml of ligroin were suspended 4.29 g of bis(2-pyridylthio)zinc and 0.41 g of zinc oxide, and the suspension was refluxed with heating for 4 hours. The reaction mixture was then filtered. The collected product was washed with three portions of 10 ml of ligroin and dried to yield 4.62 g of hexakis(2-pyridylthio)-tetrazinc monooxide as colorless powdery crystals.

Found: C, 38.87%; H, 2.53%; N, 9.10%; S, 20.30%; Zn, 27.46%.

The crystals so obtained were identical to the crystals obtained in Example 1 in the melting point, the solubilities, IR spectrum and the TGA and DSC curves.

EXAMPLE 21

In 100 ml of ethylene dichloride were suspended 5.60 g of bis(2-pyridylthio)zinc and 0.53 g of zinc oxide, and the suspension was stirred at 84°C for 4 hours. The reaction mixture was then filtered. The collected product was washed with two portions of 20 ml of ethylene dichloride and dried to yield 5.70 g of colorless powdery crystals.

Found: C, 38.13%; H, 2.74%; N, 8.89%; S, 20.23%; Zn, 27.49%.

The crystals so obtained were identical to the crystals obtained in Example 1 in the melting point, the solubilities, IR spectrum and the TGA and DSC curves.

EXAMPLE 22

In 100 ml of ethylene dichloride were suspended 4.29 g of bis(2-pyridylthio)zinc and 0.49 g of zinc hydroxide, and the suspension was refluxed with heating for 6 hours. The reaction mixture was then filtered. The collected product was washed with four portions of 10 ml of the ethylene dichloride and dried to yield 4.49 g of colorless powdery crystals.

Found: C, 38.45%; H, 2.63%; N, 8.54%; S, 20.44%; Zn, 27.51%.

The crystals so obtained were identical to the crystals obtained in Example 1 in the melting point, the solubilities, IR spectrum and the TGA and DSC curves.

EXAMPLE 23

In 100 ml of water were suspended 4.29 g of bis(2-pyridylthio)-zinc and 0.41 g of zinc oxide, and the suspension was stirred at 20°C for 50 hours. The reaction mixture was then filtered. The collected product was washed with four portions of 10 ml of water and dried to yield 4.67 g of colorless powdery crystals.

Found: C, 38.29%; H, 2.55%; N, 8.99%; S, 20.25%; Zn, 27.63%.

The crystals so obtained were identical to the crystals obtained in Example 1 in the melting point, the solubilities, IR spectrum and the TGA and DSC curves.

EXAMPLE 24

In a solution of 3.34 g of 2-pyridinethiol in 100 ml of ethylene dichloride was suspended 1.63 g of zinc oxide, and the suspension was stirred at room temperature. The reaction mixture turned pale yellow from yellow and then become colorless. After stirring for 3 hours, the reaction mixture was filtered. The collected product was washed with two portions of 20 ml of ethylene dichloride and dried to yield 4.41 g of hexakis(2-pyridylthio)tetrazinc monooxide as colorless powdery crystals. The crystals so obtained began coloring gradually at about 340°C, and decomposed and melted at 380°–385°C.

Found: C, 38.11%; H, 2.61%; N, 8.52%; S, 20.30%; Zn, 27.56%.

The crystals so obtained were identical to the crystals obtained in Example 1 in the solubilities, IR spectrum and the TGA and DSC curves.

EXAMPLE 25

In a solution of 3.34 g of 2-pyridinethiol in 100 ml of acetonitrile was suspended 1.63 g of zinc oxide, and the suspension was refluxed with heating for 6 hours with stirring. The reaction mixture was then cooled to room temperature and filtered. The collected product was washed with two portions of 20 ml of acetonitrile and dried to yield 4.54 g of hexakis(2-pyridylthio)tetrazinc monooxide as colorless powdery crystals.

Found: C, 38.18%; H, 2.49%; N, 8.96%; S, 20.47%; Zn, 27.49%.

The crystals so obtained were identical to the crystals obtained in Example 1 in the melting point, the solubilities, IR spectrum and the TGA and DSC curves.

EXAMPLE 26

In a solution of 3.34 g of 2-pyridinethiol in 100 ml of acetone was suspended 1.63 g of zinc oxide, and the suspension was refluxed with heating for 4 hours with stirring. The reaction mixture was then cooled to room temperature and filtered. The collected product was washed with two portions of 20 ml of acetone and dried to yield 4.52 g of hexakis(2-pyridylthio)tetrazinc monooxide as colorless powdery crystals.

Found: C, 38.20%; H, 2.59%; N, 8.72%; S, 20.29%; Zn, 27.67%.

The crystals so obtained were identical to the crystals obtained in Example 1 in the melting point, the solubilities, IR spectrum and the TGA and DSC curves.

EXAMPLE 27

In a solution of 3.34 g. of 2-pyridinethiol in 100 ml of ethylene dichloride was suspended 1.63 g zinc oxide, and suspension was refluxed with heating for 30 minutes with stirring. The reaction mixture was then cooled to room temperature and filtered. The collected product was washed with two portions of 20 ml of ethylene dichloride and dried to yield 4.34 g of hexakis-(2-pyridylthio)tetrazinc monooxide as colorless powdery crystals.

Found: C, 38.18%; H, 2.51%; N, 8.82%; S, 20.28%; Zn, 27.53%.

The crystals so obtained were identical to the crystals obtained in Example 1 in the melting point, the solubilities, IR spectrum and the TGA and DSC curves.

EXAMPLE 28

To a solution of 3.34 g of 2-pyridinethiol in 100 ml of ethylene dichloride was added 2.09 g of zinc hydroxide (purity 95%), and the mixture was stirred at room temperature for 30 hours. The reaction mixture was then filtered. The collected product was washed with three portions of 20 ml of ethylene dichloride and dried to yield 4.09 g of hexakis(2-pyridylthio)-tetrazinc monooxide as colorless powdery crystals.

Found: C, 38.06%; H, 2.54%; N, 8.63%; S, 20.08%; Zn, 27.38%.

The crystals so obtained were identical to the crystals obtained in Example 1 in the melting point, the solubilities, IR spectrum and the TGA and DSC curves.

EXAMPLE 29

To 60 ml of water were added 3.34 g of 2pyridinethiol and 40 ml of 1N aqueous sodium hydroxide solution. After a homogeneous solution was obtained, a solution of 5.95 g of zinc nitrate · 6 hydrates in 20 ml of water was added dropwise thereto at room temperature for 5 minutes. The mixture was stirred at room temperature for 6 hours and filtered. The collected product was washed with five portions of 30 ml of water and dried to yield 4.35 g of hexakis(2-pyridylthio)tetrazinc monooxide as colorless powdery crystals.

Found: C, 38.19%; H, 2.48%; N, 8.90%; S, 20.46%; Zn, 27.51%.

The crystals so obtained were identical to the crystals obtained in Example 1 in the melting point, the solubilities, IR spectrum and the TGA and DSC curves.

EXAMPLE 30

To a solution of 3.34 g of 2-pyridinethiol and 2.12 g of sodium carbonate in 80 ml of water was added dropwise at room temperature a solution of 5.95 g of zinc nitrate · 6 hydrates in 20 ml of water. The mixture was stirred at room temperature for one hour and filtered. The collected product was washed with five portions of 30 ml of water and dried to yield 4.33 g of hexakis(2-pyridylthio)tetrazinc monooxide as colorless powdery crystals.

Found: C, 38.70%; H, 2.58%; N, 9.01%; S, 20.46%; Zn, 27.46%.

The crystals so obtained were identical to the crystals obtained in Example 1 in the melting point, the solubilities, IR spectrum and the TGA and DSC curves.

EXAMPLE 31

To a solution of 3.40 g of zinc chloride in 100 ml of water were successively added 5.56 g of 2-pyridinethiol and a solution of 3.00 g of sodium hydroxide in 50 ml of water. The mixture was stirred at room temperature for 17 hours and filtered. The collected product was washed with five portions of 30 ml of water and dried to yield 5.35 g of hexakis(2-pyridylthio)tetrazinc monooxide as colorless powdery crystals.

Found: C, 38.17%; H, 2.47%; N, 8.72%; S, 20.40%; Zn, 27.66%.

The crystals so obtained were identical to the crystals obtained in Example 1 in the melting point, the solubilities, IR spectrum and the TGA and DSC curves.

EXAMPLE 32

To a solution of 1.70 g of zinc chloride in 40 ml of water was added a solution of 2.78 g of 2-pyridinethiol and 1.5 g of sodium hydroxide in 60 ml of water. The mixture was stirred at room temperature for 17 hours and filtered. The collected product was washed with five portions of 30 ml of water and dried to yield 2.76 g of hexakis(2-pyridylthio)tetrazinc monooxide as colorless powdery crystals.

Found: C, 38.49%; H, 2.55%; N, 8.77%; S, 20.53%; Zn, 27.69%.

The crystals so obtained were identical to the crystals obtained in Example 1 in the melting point, the solubilities, IR spectrum and the TGA and DSC curves.

EXAMPLE 33

To a solution of 3.34 g of 2-pyridinethiol and 2.64 g of potassium hydroxide in 80 ml of water and added dropwise a solution of 2.73 g of zinc chloride in 20 ml of water. The mixture was stirred at room temperature for 30 minutes and filtered. The collected product was washed with five portions of 30 ml of water and dried to yield 4.17 g of hexakis(2-pyridylthio)tetrazinc monooxide as colorless powdery crystals.

Found: C, 38.00%; H, 2.53%; N, 8.98%; S, 20.09%; Zn, 27.53%.

The crystals so obtained were identical to the crystals obtained in Example 1 in the melting point, the solubilities, IR spectrum and the TGA and DSC curves.

EXAMPLE 34

To 40 ml of water were successively added 3.34 g of 2-pyridinethiol and 40 ml of 1N aqueous sodium hydroxide solution, and, after a homogeneous solution was obtained, a solution of 4.39 g of zinc acetate in 20 ml of water was added dropwise thereto. The mixture was stirred at room temperature for one hour and filtered. The collected product was washed with five portions of 30 ml of water and dried to yield 4.52 g of hexakis(2-pyridylthio)tetrazinc monooxide as colorless powdery crystals.

Found: C, 38.12%; H, 2.53%; N, 8.81%; S, 20.32%; Zn, 27.49%.

The crystals so obtained were identical to the crystals obtained in Example 1 in the melting point, the solubilities, IR spectrum and the TGA and DSC curves.

EXAMPLE 35

To a solution of 3.34 g of 2-pyridinethiol and 4.04 g of triethylamine in 100 ml of 95% ethanol was added dropwise a solution of 2.73 g of zinc chloride in 50 ml of ethanol. The mixture was stirred at room temperature for 12 hours and filtered. The collected product was washed with 50 ml of ethanol and dried to yield 4.49 g of hexakis(2-pyridylthio)-tetrazinc monooxide as colorless powdery crystals.

Found: C, 38.23%; H, 2.61%; N, 8.93%; S, 20.40%; Zn, 27.53%.

The crystals so obtained were identical to the crystals obtained in Example 1 in the melting point, the solubilities, IR spectrum and the TGA and DSC curves.

REFERENCE EXAMPLE 1

In a mixture of 0.09 g of water and 100 ml of 1,4-dioxane was suspended 5.71 g of bis(2-pyridylthio)-zinc. The suspension was stirred at 80°C for 7 hours and filtered at 80°C. The collected product was washed with 40 ml of 1,4-dioxane at 20°C and dried to yield 5.32 g of a colorless powder. The obtained powder was identified as a mixture of bis(2-pyridylthio)zinc and hexakis(2-pyridylthio)tetrazinc monooxide by the IR spectrum.

The filtrate and washing were combined. After evaporation of 1,4-dioxane under reduced pressure, to this residue was added 100 ml of acetone. The mixture was then stirred for 10 minutes and filtered leaving the insoluble materials. The filtrate was concentrated under reduced pressure to give 0.33 g of 2-pyridinethiol as yellow crystals, m.p. 127°– 128°C.

REFERENCE EXAMPLE 2

To 100 ml of 1,4-dioxane were added 4.69 g of hexakis(2-pyridylthio)tetrazinc monooxide and 1.11 g of 2-pyridinethiol. The mixture was stirred at 80°C for 7 hours and filtered at 80°C. The collected product was washed with 40 ml of 1,4-dioxane at 20°C and dried to yield 5.33 g of a colorless powder. The powder so obtained was identified as a mixture of bis(2-pyridylthio)zinc and hexakis(2-pyridylthio)tetrazinc monooxide by the IR spectrum.

The filtrate and washing were combined. After evaporation of 1,4-dioxane under reduced pressure, to this residue was added 100 ml of acetone. The mixture was then stirred for 10 minutes and filtered leaving the insoluble materials. The filtrate was concentrated under reduced pressure to give 0.30 g of 2-pyridinethiol as yellow crystals, m.p. 127°–128°C.

As is clear from Reference examples 1 and 2, two reactions, that is, the reaction of the starting compounds, bis(2-pyridylthio)zinc and water, and the reaction of the resulting products, hexakis(2-pyridylthio)tetrazinc monooxide and 2-pyridinethiol, gave the same reaction mixture when these reactions were carried out under the same reaction conditions by adopting the molar ratio based on the reaction equation. These results mean that the reaction of bis(2-pyridylthio)zinc and water is reversible.

The following references are placed for further confirmation.

REFERENCE EXAMPLE 3

In 120 ml of benzene were suspended 5.00 g of hexakis-(2-pyridylthio)tetrazinc monooxide and 1.18 g of 2-pyridinethiol. The suspension was refluxed with removal of water produced, by azeotropic distillation with benzene. The aqueous benzene removed out of the reaction mixture was subjected to phase-separation to expel the water, and the remaining benzene was returned to the reaction mixture while the reaction was continued. After the reaction for 6 hours, the reaction mixture was filtered. The collected product was washed with 50 ml of benzene and dried to yield 5.98 g of bis(2-pyridylthio)zinc as slightly yellowish crystals. The crystals so obtained were identified by the elemental analysis and the IR spectrum.

Found: C, 41.89%; H, 2.83%; N, 10.28%; S, 22.08%; Zn, 22.19%.

Calcd. for $C_{10}H_8N_2S_2Zn$: C, 42.04%; H, 2.82%; N, 9.81%; S, 22.45%; Zn, 22.08%.

In the benzene filtrate obtained above, 2-pyridinethiol was not found.

REFERENCE EXAMPLE 4

In 115 ml of water was suspended 5.71 g of bis(-2pyridylthio)zinc, and the suspension was stirred at 30°C for 50 hours and filtered. The collected product was washed with two portions of 20 ml of water and dried to yield 5.43 g of slightly yellowish powder. The powder so obtained was identified as a mixture of bis(2-pyridylthio)zinc and hexakis(2-pyridylthio)tetrazinc monooxide by the IR spectrum.

The filtrate and washings obtained in the aforementioned filtration were combined and concentrated under reduced pressure. To the residue was added 100 ml of acetone, and the mixture was stirred for 10 minutes and filtered leaving the insoluble materials. The filtrate was then concentrated under reduced pressure to give 0.29 g of 2-pyridinethiol as yellow crystals, m.p. 125°–127°C.

The usefulness of the present 2-pyridylthiozinc-oxide complex, hexakis(2-pyridylthio)tetrazinc monooxide, will be seen from the following examples, in which the term "part" means "weight part". The term "M.I." means "Melt Flow Index" determined in accordance with ASTMD 1238.

The notations shown in the examples mean the following anti-deteriorating agents and antioxidizing agents.

Anti-deteriorating agent

A: Hexakis(2-pyridylthio)tetrazinc monooxide (included in the present invention)

a: MARK-CDA-1 (trade name: Adeka-Argus Chemical Industry Co., Ltd.) (supposed to be an acid amide type compound based on IR absorptions assigned to amide, $NH_2$ and phenyl groups)

b: N,N'-Dibenzylideneoxalic acid dihydrazide (trade name: Eastman Inhibitor OABH, Eastman Kodak Co.)

c: N-Salicylidenesalicylic acid hydrazide (trade name: Chel - 180, Ciba-Geigy Co.)

Anti-oxidizing agent d: 2.6-Di-tert-butyl-4-methylphenol e: Tetrakis[methylene 3-(3,5-di-tert-butyl-4-hydroxy-phenyl)propionate]methane f: 1,3,5-Trimethyl-2,4,6-tris(3,5-di-tert-butyl-4-hydroxybenzyl)benzene

EXAMPLES 36 – 40

1. Preparation of test pliece

Into a Brabender Plastograph (available from Brabender Corporation, West Germany) adjusted to 60 r.p.m. of the rotation speed and a temperature of 140°C were charged 100 parts of ethylene homopolymer (M.I. = 0.2) with no additives prepared by a high pressure process. Two minutes later, 0.10 part of an anti-oxidizing agent (e) and a fixed amount of the anti-deteriorating agent (A) were added thereto. Further, another 2 minutes later, 0.10 part of copper stearate was added to the mixture, which was subsequently kneaded for 8 minutes. The mixture was then heated on a plate of 190°C for 1 minute and pressed at a pressurre of 300 kg/cm² for 1 minute by means of the spacer to form a film having a thickness of 0.25 mm. A round film of 4 mm in diameter was prepared by punching of the obtained film, and employed as a test pliece.

2. Determination of anti-deterioration effect

The time required for appearance of a peak showing generation of heat caused by oxidation was determined by means of Standard-Type Rapidly Fluctuating Differential Calorimeter (available from Rigaku Denki Kogyo Ltd., Japan). A test piece was placed in one sample dish of the calorimeter, the other dish being empty. After the atmosphere of the calorimeter was replaced with oxygen, the environmental temperature was elevated to 195°C in about 5 – 10 seconds by means of inside heating system, then elevated to 200°C in about 30 seconds and kept at this temperature, during which process oxygen was made to flow therethrough at a rate of 180 ml/min. The induction period herein means the period from the time when the temperature rose to 200°C to the time when there appeared a peak showing generation of heat caused by oxidation of a test piece. The period determined as above was adopted to estimate an anti-deterioration effect.

The results obtained according to the above-mentioned procedure are shown in Table 1.

Table 1

| Example | Anti-deteriorating Agent | Amount (part) | Induction Period (min.) |
| --- | --- | --- | --- |
| 36 | A | 0.050 | 34 |
| 37 | A | 0.075 | 68 |
| 38 | A | 0.100 | 90 |
| 39 | A | 0.150 | 167 |
| 40 | A | 0.500 | 494 |

EXAMPLES 41 – 47 (COMPARATIVE EXAMPLES)

Test pieces were prepared by the procedure described in Examples 36 – 40 except for using no anti-deteriorating agent (A) and no copper stearate, using no anti-deteriorating agent (A), or using the known anti-deteriorating agent in an amount shown in Table 2, instead of the anti-deteriorating agent (A) of this invention. Their characteristics were determined in the manner described in Examples 36 – 40 and the results are shown in Table 2.

Table 2

| Example | Anti-deteriorating Agent Amount (part) | Copper Stearate Amount (part) | Induction Period (min.) |
| --- | --- | --- | --- |
| 41 | — | — | 39 |
| 42 | — | 0.10 | 0 |
| 43 | a | 0.05 | 0.10 | 10 |
| 44 | a | 0.10 | 0.10 | 20 |
| 45 | a | 0.15 | 0.10 | 34 |
| 46 | b | 0.15 | 0.10 | 36 |
| 47 | c | 0.15 | 0.10 | 40 |

EXAMPLES 48 – 49

Into the Brabender Plastograph adjusted to 60 r.p.m. of the rotation speed and a temperature of 190°C were charged 100 parts of isotactic polypropylene (M.I. = 5) into which was previously incorporated 0.30 part of the anti-oxidizing agent (d) and 0.08 part of the anti-deteriorating agent (e). Two minutes later, a fixed amount of the anti-deteriorating agent (A) was added thereto. Further, another 2 minutes later, 1.0 part of copper powder or 0.2 part of copper stearate was added to the mixture, which was subsequently kneaded for 8 minutes. The mixture was then heated on a plate of 190°C for one minute and was pressed at a pressure of 100 kg/cm² for one minute by means of the spacer to form a film having a thickness of 1.0 mm. The obtained film was cut into five strips (each 50 mm × 30 mm).

The five strips were placed in a Geer's Oven (Inside temperature 150°C, with a deviation of ±1°C), and periods required for yellowing and deteriorating the strips were determined. The thus obtained periods are regarded as Heat Stable Durations, and the shortest and longest durations are both shown in Table 3.

EXAMPLES 50 – 53 (COMPARATIVE EXAMPLES)

Test pieces were prepared by the procedure described in Examples 48 – 49 except for using no anti-deteriorating agent (A) or using the known anti-deteriorating agent in an amount shown in Table 3, instead of the anti-deteriorating agnet (A) of this invention. Their characteristics were determined in the manner described in Examples 48 – 49 and the results are shown in Table 3.

Table 3

| Example | Anti-deteriorating Agent Amount (part) | Copper Powder or Copper Stearate | Heat Stable Duration (day) |
| --- | --- | --- | --- |
| 48 | A | 0.40 | Powder | 38 – 41 |
| 49 | A | 0.40 | Stearate | 17 – 20 |
| 50 | — | | Powder | 7 – 9 |
| 51 | — | | Stearate | 1 – 2 |
| 52 | b | 0.40 | Powder | 20 – 22 |
| 53 | b | 0.40 | Stearate | 3 – 4 |

EXAMPLE 54

Into the Brabender Plastograph adjusted to 60 r.p.m. of the rotation speed and a temperature of 140°C were charged 100 parts of ethylene homopolymer (M.I. = 0.2) with no additives prepared by a high pressure process. Two minutes later, 0.10 part of the anti-deteriorating agent (A) was added thereto, and the mixture was subsequently kneaded for 10 minutes. The mixture was then heated on a plate of 190°C for one minute and pressed at a pressure of 300 kg.cm² for one minute by means of the spacer to form a film having a thickness of 0.25 mm. A round film of 4 mm in diameter was prepared by punching of the obtained film, and employed as a test piece.

The determination of the characteristics was carried out in the same manner as in Examples 36 – 40, and an induction period of 15 minutes was given.

EXAMPLES 55 – (COMPARATIVE EXAMPLE)

Test pieces were prepared by the procedure described in Example 54 except for using no anti-deteriorating agent (A) (Example 55) or using 0.10 part of the anti-oxidizing agent (f), instead of the anti-deteriorating agent (A) (Example 56). The determination of the characteristics was carried out in the same manner as Example 54, and induction periods of 0 and 5 minutes were given respectively.

What is claimed is:

1. A stabilized polyolefin composition which comprises 100 weight parts of a polyolefin and 0.001 – 5 weight parts of hexakis(2-pyridylthio)tetrazinc monooxide having the formula

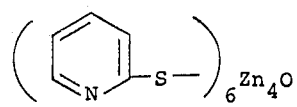

2. A stabilized polyolefin composition as claimed in claim 1, wherein the hexakis(2-pyridylthio)tetrazinc monooxide is used in 0.01 – 3 weight parts based on 100 weight parts of the polyolefin.

3. A stabilized polyolefin composition as claimed in claim 1, wherein the polyolefin is selected from the class consisting of homopolymers and copolymers of ethylene, propylene, butene-1-isobutene, pentene-1 and 4-methylpentene-1, copolymers of these olefins and either methyl or ethyl acrylate or methyl or ethyl methacrylate, copolymers of these olefins and vinyl acetate, mixtures of these polymers, liquid amorphous polypropylene and liquid amorphous polybutene.

4. A stabilized polyolefin composition as claimed in claim 1, wherein the polyolefin is selected from the class consisting of an ethylene homopolymer, isotactic polypropylene and an ethylene-vinyl acetate copolymer.

5. A stabilized polyolefin composition as claimed in claim 1, which further comprises one or more of a conventional stabilizer, dispersing agent, plasticizer, anti-static agent, filler and pigment.

* * * * *

UNITED STATES PATENT AND TRADEMARK OFFICE
CERTIFICATE OF CORRECTION

PATENT NO. : 3,962,178
DATED : June 8, 1976
INVENTOR(S) : MITSUO MASAKI et al

It is certified that error appears in the above-identified patent and that said Letters Patent are hereby corrected as shown below:

(1) Column 3, line 11: replace "by-procuct" with --- by-product ---.

(2) Column 6, line 52: delete "pressure piece".

(3) Column 10, line 25: before "obtained", replace "as" with --- so ---.

(4) Column 25, line 8: replace "butene-1-isobutene" with --- butene-1, isobutene ---.

Signed and Sealed this

Eighth Day of February 1977

[SEAL]

Attest:

RUTH C. MASON
Attesting Officer

C. MARSHALL DANN
Commissioner of Patents and Trademarks